US008421636B2

(12) United States Patent (10) Patent No.: US 8,421,636 B2
Collette et al. (45) Date of Patent: Apr. 16, 2013

(54) PATIENT MONITORING SYSTEM

(76) Inventors: Daniel R. Collette, Benouville (FR); Matthew Peter Napier, Albuquerque, NM (US)

(*) Notice: Subject to any disclaimer, the term of this patent is extended or adjusted under 35 U.S.C. 154(b) by 77 days.

(21) Appl. No.: 10/835,915

(22) Filed: Apr. 30, 2004

(65) Prior Publication Data

US 2005/0033250 A1 Feb. 10, 2005

Related U.S. Application Data

(60) Provisional application No. 60/466,944, filed on Apr. 30, 2003, provisional application No. 60/520,240, filed on Nov. 12, 2003.

(51) Int. Cl.
*G08B 21/00* (2006.01)
*G08B 1/08* (2006.01)
*G08B 23/00* (2006.01)
*A61F 13/20* (2006.01)

(52) U.S. Cl.
USPC ............ 340/604; 340/539.12; 340/573.1; 340/573.5; 340/602; 604/361

(58) Field of Classification Search .......... 340/602–604, 340/539.12, 573.1, 573.5; 604/361
See application file for complete search history.

(56) References Cited

U.S. PATENT DOCUMENTS

| 4,834,733 A * | 5/1989 | Huntoon et al. ............ 604/361 |
| 6,373,395 B1 * | 4/2002 | Kimsey ...................... 340/602 |
| 6,617,488 B1 * | 9/2003 | Springer et al. ............ 604/361 |
| 6,970,091 B2 * | 11/2005 | Roe ............................ 340/573.1 |
| 2003/0130631 A1 * | 7/2003 | Springer et al. ............ 604/361 |
| 2003/0137425 A1 * | 7/2003 | Gabriel ...................... 340/573.5 |
| 2004/0100376 A1 * | 5/2004 | Lye et al. .................. 340/539.12 |

* cited by examiner

*Primary Examiner* — Daniel Wu
*Assistant Examiner* — Mancil Littlejohn

(57) ABSTRACT

A patient monitoring system according to one embodiment includes a real-time wetness sensor configured to detect the rate of change in wetness occurring within an associated diaper, and automatically adjusting the sensitivity of the sensor to account for a wetness event unrelated to urination. A monitoring unit may be utilized in such a manner that the monitoring system controller-monitors the wetness sensor and generates data associated with detected-wetness events relative to the diaper. A wireless transmitter configured with the monitoring unit and in communication with the monitoring system controller may be further utilized to send the generated data, through a host computer, to a caregiver unit having a caregiver system controller in communication with the host computer. The caregiver can then check the status of the patient, provide a service, and annotate the patients history by transmitting the recorded observation and service provided back to the base station.

32 Claims, 14 Drawing Sheets

DIAPER WET WIRING

ALL OTHER SENSORS WIRING

PATIENT MONITORING SYSTEM

CROSS REFERENCE TO RELATED APPLICATIONS

This application claims the priority of Provisional Patent Applications Nos. 60/466,944, filed Apr. 30, 2003, and 60/520,240, filed Nov. 12, 2003, the entire contents of which are incorporated by reference herein.

STATEMENT REGARDING FEDERALLY SPONSORED RESEARCH OR DEVELOPMENT

Not Applicable

DESCRIPTION OF ATTACHED APPENDIX

This application contains a computer program listing appendix, the entire contents of which are incorporated herein by reference, which contains the following:

| File Name | Date of Creation | Size |
|---|---|---|
| "caregiver module.txt" | Apr. 28, 2004 | 23 KB |
| "infant module.txt" | Apr. 28, 2004 | 6 KB |
| "mommy module.txt" | Apr. 28, 2004 | 6 KB |
| "patient module.txt" | Apr. 28, 2004 | 10 KB |

BACKGROUND OF THE INVENTION

1. Field of the Invention

The present invention relates generally to a patient monitoring system, and in particular, to a patient monitoring system that permits accurately detailed wetness sensing and integrated caregiver management.

2. Description of the Related Art

There are numerous devices and systems targeted to the problem of detecting and reporting wetness in a diaper or similar article. None of these systems have earned wide commercial success. Accuracy is both a persistent problem for these market participants and a heretofore unrecognized opportunity for a product that is able to detect for wetness in a diaper in a way that accounts for a variety of problems.

A number of devices and wetness detecting systems have been attempted to report when a diaper, bedding, or adult incontinence article becomes wet due to incontinence. These devices frequently report erroneous detection wet incontinent related conditions due to a variety of problems, such as: perspiration generated by the wearer of the article; fluctuations in electrostatic capacity caused, for example, by movement of the wearer of the diaper; and even climatic differences that may cause excess humidity in the diaper or similar article.

Patients and other users of diapers with bladder incontinence often share other infirmities that require the frequent attention of a caregiver. Devices that provide false wetness indications may result in a lower quality of care for the patient if the caregiver becomes conditioned to frequent erroneous reports of wetness and therefore neglects to provide a reasonable standard of care.

Some have approached this problem with attempts at permitting a nominal level of integrated caregiver management facility to this problem. These systems often focus on the passive participation of the caregiver and neglect the opportunity to fully engage the caregiver as an active participant in addressing the direct and related needs of incontinent patients, thereby missing the chance to raise the quality of care for the patient.

BRIEF SUMMARY OF THE INVENTION

The primary object of the invention is to provide a diaper with an improved wetness detector.

Another object of the present invention is to provide an improved wetness detector that can monitor the rate of change of the level of wetness in an article A further object of the present invention is to provide real-time wetness sensing that can automatically adjust sensitivity to account for otherwise false or erroneous wetness events such as static electricity, movement, humidity, and the like.

A still further object of the present invention is to detect other patient infirmities or problems related to their incontinent condition.

Yet another object is to provide a patient monitoring system where the quality of care and degree of accountability of caregivers is improved, by integrating them into the monitoring-information system through their recording of observations and services provided to patients.

Other objects and advantages of the present invention will become apparent from the following descriptions, taken in connection with the accompanying drawings, wherein, by way of illustration and example, an embodiment of the present invention is disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

This invention will be better understood by referring to the accompanying drawings, wherein.

DETAILED DESCRIPTION OF THE PREFERRED EMBODIMENTS

Figure 1:
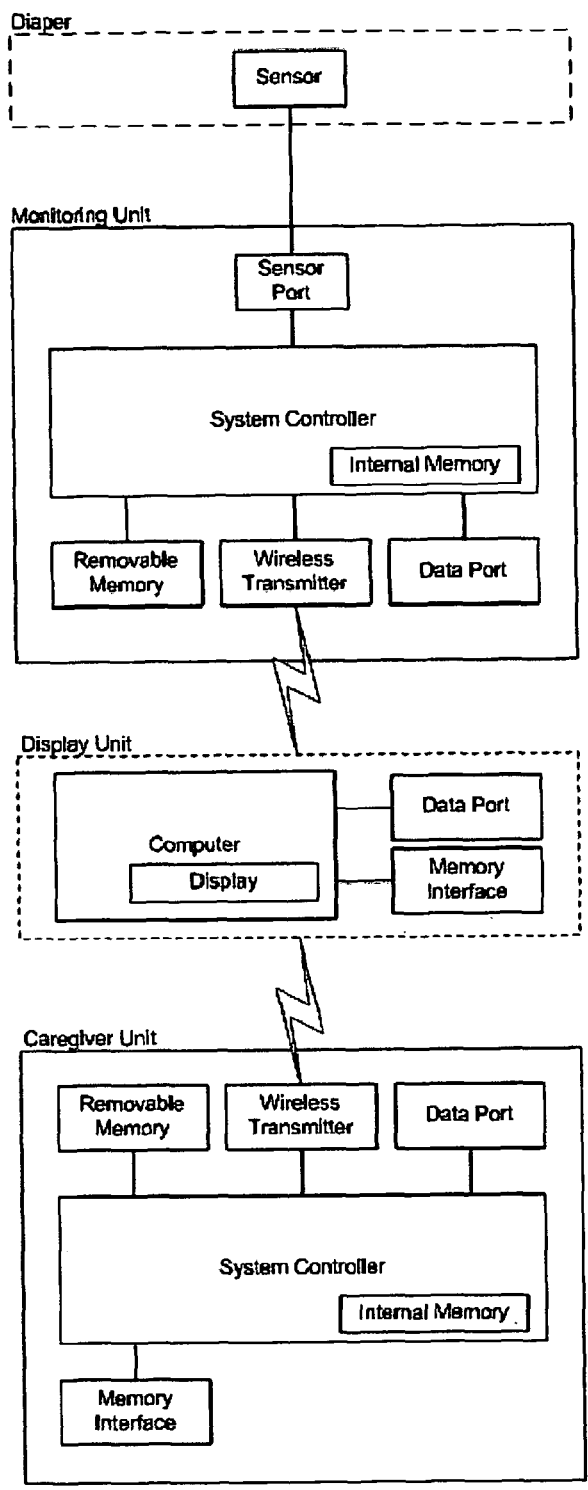
FIG. 1 is a block diagram showing one embodiment of the present invention.
Figure 2:
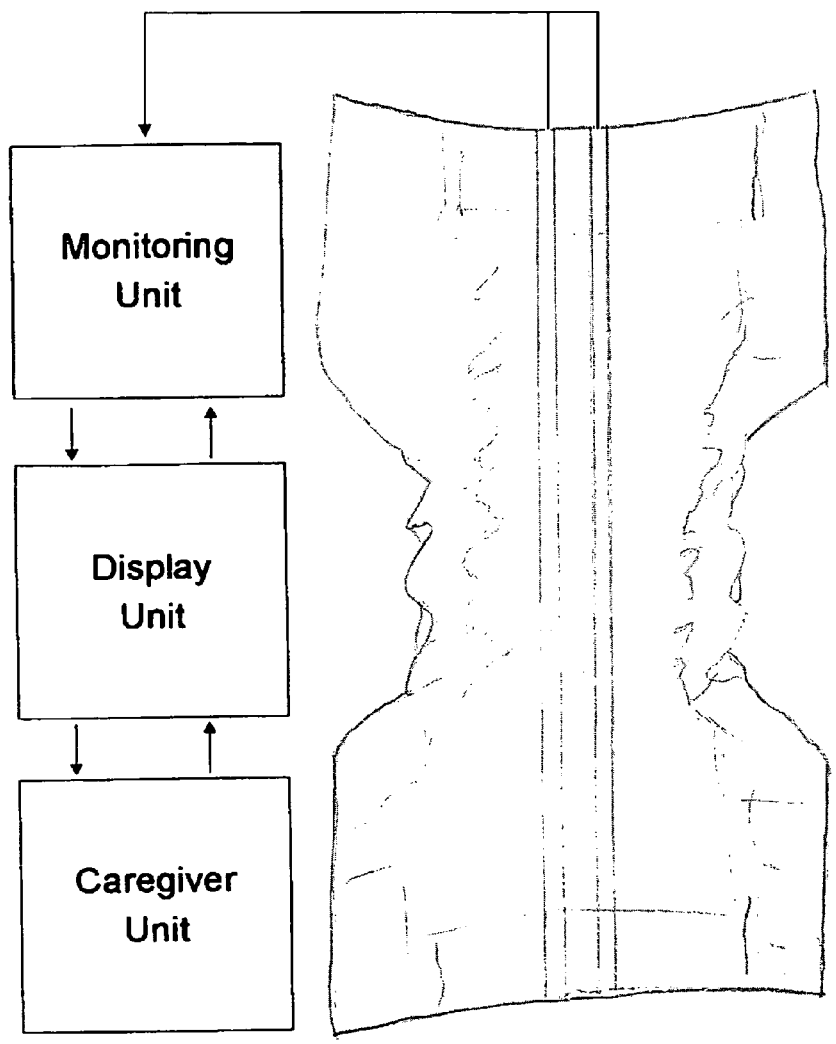
FIG. 2 is a detailed view of a preferred sensor implementation according to one embodiment of the present invention.
Figure 3:
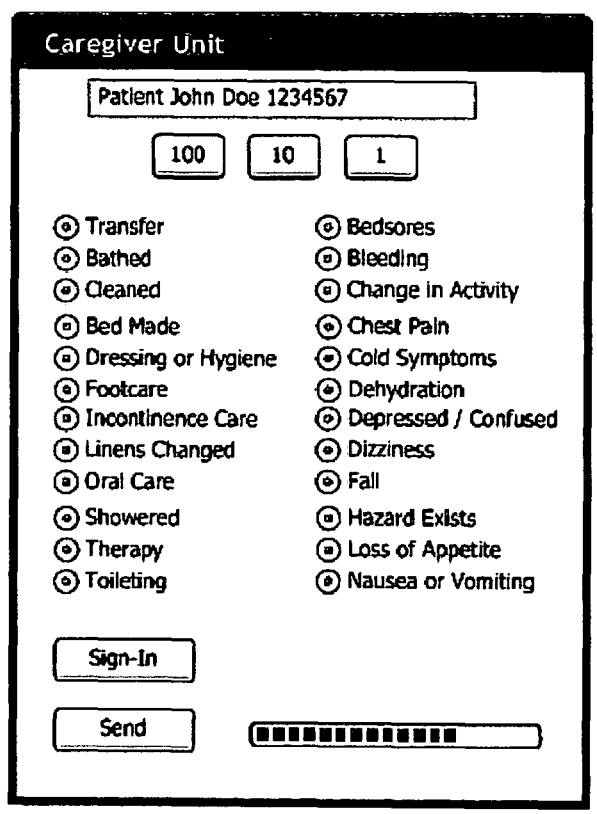
FIG. 3 is a diagram of a caregiver unit having several user interface features in accordance with some embodiments of the present invention.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

As used herein, the term "diaper" refers to garments or pads which are placed against or in proximity to the body of the wearer to absorb and contain the various fluids discharged from the body. A non-exhaustive list of examples of absorbent articles includes diapers, diaper covers, disposable diapers, training pants, pants-type diapers, feminine hygiene products, and adult incontinence products.

The terms "base station", "display unit", "host", and "host computer" as used herein interchangeably, and all refer to a computer or computing device for displaying, recording, and/or managing data.

The terms "wetness" and "wetness event" are to be understood as including human urination, defecation, and other bodily discharge events.

The following descriptions are of various embodiments of the present invention.

Infant Diaper Sensor

This system is to notify when a diaper becomes wet. The sensing materials have been refined to aluminum and polymer backing and conductive thread. The novel electronics offers the capability to sense in real-time with adjustable measurement capability. It can change the level of the comparator and account for static and other transient effects. It is these effects which have really been the cause that no system has been effective on the market to date, particularly in disposables which generate significant levels of static.

The method of connecting the sensor to the diapers is currently with snaps. However, flex connectors and Velcro sewn with the conductive thread can also be used. In this case, the electronics would just fasten over the Velcro portion of the waist of the disposable and make the connection directly to the conductive thread.

Any of the standard means of notification can be used with this system, including, alarms, bells, whistles, recorded playback, RF transmission to a remote-site.

Toilet Training

The basic concept is to toilet train a child. The system will work with disposables, toilet training cotton pants, or any other clothing. The concept is to create a link for the child between wetting and the toilet. The problem with toilet training is that children are found wet after the fact and do not have sufficient cognitive abilities to connect an event that happened 10 minutes earlier with what the parents are saying in the present. The concept is to provide instant notification of wetting so that parents or caregivers can then take the child to the bathroom to finish going to the bathroom in the toilet, or to discuss that what just happened in their diaper needs to happen in the toilet.

Electronics and connections are the same as in the diaper notification. There is a record and playback option on this system, where a parent or caregiver can record a short message to be played upon wetting, such as "don't wet in your diaper, come find me and I will take you to the toilet." This makes the connection to the present event immediate and significant.

Daycare Center System

This system is developed specifically to permit the caregivers to know immediately that a child in the daycare is wet. The novel component to this system is that the software allows for the system to accommodate all the children in a daycare with only a single receiver. Each child has a coded transmitter and the system can decode that transmission to the individual child. Normally, this transfer is a 1:1 system. In this case, it is 1000:1. This is critical because of cost considerations.

Following is a brief of the RF system used, although there are other frequencies and systems that could be developed. This system uses 418 MHz and a transmit or no transmit system. This is important because FCC rules consider the total transmit time in their power calculations, and since less that half of the transmission time is off (that is, data is being sent while in the off state) the system can have significantly higher power and resultant range that current 802.11 or WIFI applications. One of the features of the system that is most appreciated is the fact that pictures pop-up on the screen showing the child or children who are wet. The transmitted data is encoded into the xilinx chip at the transmitter, and the bits are serially streamed to the transmitter at 1 KHz rate. This rate can be adjusted and changed if needed. There is also no limit to the length of the bit stream being transmitted. Programmable features of the xilinx chip allow for significant savings in power because the chip can shutdown everything but the oscillator while waiting for a wet event. Even in the most simple existing circuits the battery life is significantly shorter because the comparator and oscillator are continuously running and don't have sleep features.

All of the advantages of using real-time as explained earlier apply to this application as well. This chip also allows smart programming such as verifying when the diaper has been changed and that a diaper is attached and not the system merely disconnected. It also automatically retransmits updates when the status of the unit changes (i.e., wet, disconnected, new dry diaper), and can be programmed to trigger at subsequent wettings without changing on the initial wetting.

Bedwetting Unit

This unit can use normal garments with the sensor sewn into a liner, or it can be disposable such as a pullup. This unit is a wireless RF unit having the same transmitter and functions as the Patient Monitoring System. It has additional electronics to make it re-chargeable and in fact the transmitter and sensing unit worn by the enfant would during the daytime hours, be placed into the bedside unit which would have not only the alarm and transmitter, but also a recharger stand and electronics.

The basic operation is wetness sensing, transmission to a bedside stand, which would be plugged into an electrical socket. The bedside unit has the high decibel, alarm along with a reset button. The bedside unit further includes the receiving antenna and a repeater, which would re-transmit the alarm signal to a remote beside unit in the parents or caregivers room. The bedside also has additional programmable features, such as an alarm clock which can be set to awaken the bedwetter prior to the normal time which he wets each night. It is also programmable for decibel level, a voice recording that would call the bedwetter by name and not just an sound alarm, since the bedwetter usually wakes quicker when they are called by name, it could also have a light incorporated in it, and this light can be programmed as with the alarm.

The unit in the parents or caregivers room is the receiver and alarm with reset. If the child wakes up on his own and resets his bedside unit, the parents unit automatically resets, letting them know that the child is up and taking care of things. The transmitter for the child has the capability of automatically determining whether it is disconnected or attached to a dry sensor. It can also calibrate at each reset with the body mass of the wearer to hold in memory a real-time capacitance measure that ensures the diaper is being worn and not just attached to an empty diaper.

Assisted Living Center/Daycare Centers

Patient Unit

The patient unit is worn by the patient. It has wetness sensing capability in real-time. In addition, it contains a magnetic switch used to record visits to the wearer, it has motion detection capability, fall indicator, leaving a restricted area indicator, GPS locator capability, a call button and an emergency call button. Some of these actions are activated by the wearer and others are activated externally or automatically. All data is transmitted by RF to the basestation using the same serial transmission function described previously.

Caregiver Unit

The caregiver unit is a handheld application. The caregiver can select the patient ID or room number, care that has been given and observations. The care and observations can be adapted to the needs of the facility. Once selected, an LED lights up indicating that the action has been selected. Once the caregiver has selected all the appropriate services which have been rendered and observations made, a send button is pushed and the appropriate information is sent by RF to the base station. The caregiver unit is icon driven and requires no English or particular language skill. The application could just as easily be prepared on a handheld however and interfaced to the same base unit. This handheld is easily programmed to various languages or application icons changed by selection from a menu.

The handheld also receives input from the base station indicating critical patient status, or next item in the queue on the handheld screen. The handheld also records which caregiver gave the service or observation and date and time stamps.

The base station is comprised on the receiver and software. The caregiver unit's digital output is fed serially into the computer where the software decodes the information and appends the appropriate services and observations to the patient's record.

The base station also records events which need attention to the screen or handheld of the caregivers. The screen is prioritized according to time of event and critical nature of the event. When the event has been taken care of, it is automatically removed from the queue.

The base station further logs all diaper activity. The base station provides reports on diaper use and changing statistics, displays the current diaper status of all babies and their name and picture. Users can customizes the number of insults before a change is required for each baby. It further logs all diapers used and automatically fills out an order form for new diapers. Provides audio and visual notification of all new diaper activity. Automatically keeps detailed records all requests for care and services provided for each individual.

Mommy Unit

The mommy unit is an RF unit between the infant and the mother. The infant has the normal detection unit comprised of the xilinx PLD and detectors but in addition to the output of tune, recorded message, LED, etc, it also has an RF transmitter. When the RF transmitter is selected, all the other output means are disabled. The RF is transmitted to a unit which the mother has. It can be set to beep tune, or vibrate. Any of the standard notification modes. When the child becomes wet, the mother is immediately notified by one of the means described. The mommy unit as with all the mobile receiver units will have a RF level detection circuit that allows the portable receiver to be powered down until the initial RF burst detected by a parallel diode scheme. The DC component generated by a RF burst through this diode combination is used to "wake up" the receiver for the incoming transmitted serial bit stream.

The mommy unit allows for toilet training and wet diapers to be monitored in a public setting without embarrassment to child or parent and at the same time without interrupting toilet training or care to the infant.

The following detailed descriptions are of the preferred embodiments of the present invention.

Assisted Living Center/Daycare Centers

Patient Module

Figure 4:
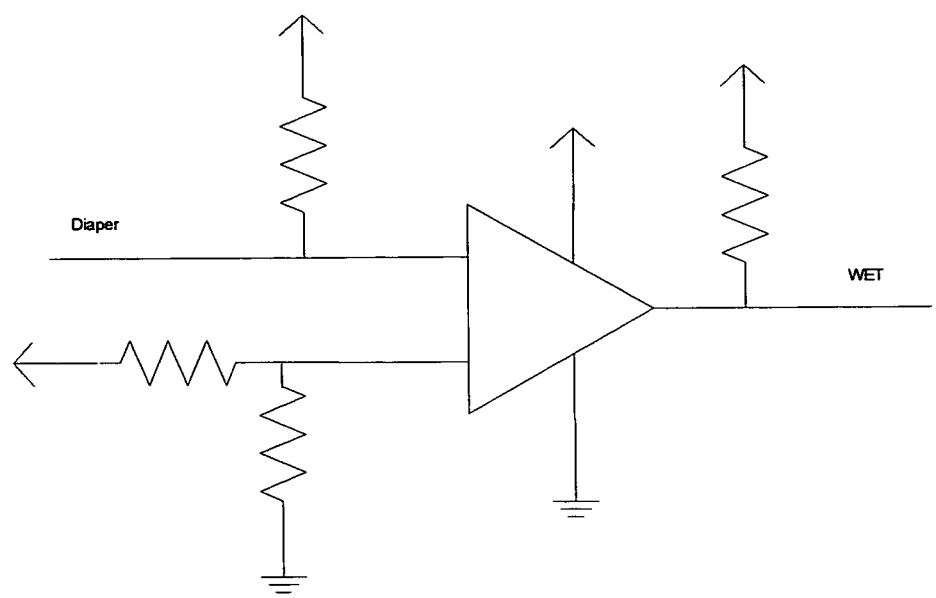
FIG. 4 representatively shows a schematic circuit diagram of a resistor divider network that can be employed with the present invention.
Figure 5:
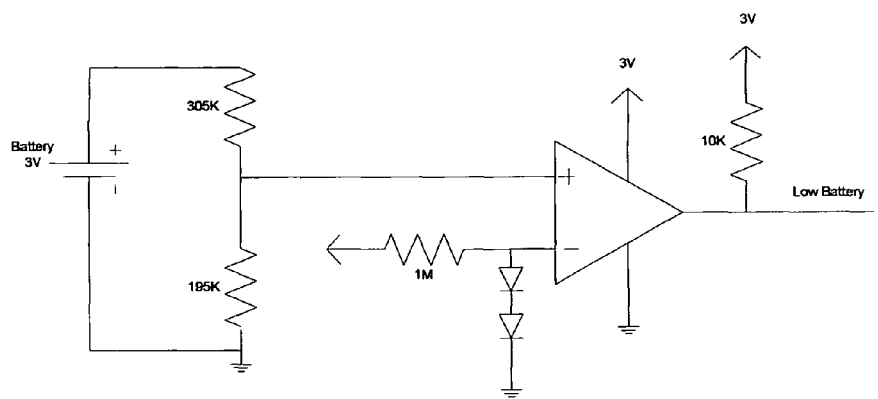
FIG. 5 representatively shows a schematic circuit diagram of a low battery detector that can be employed with the present invention.
Figure 6:
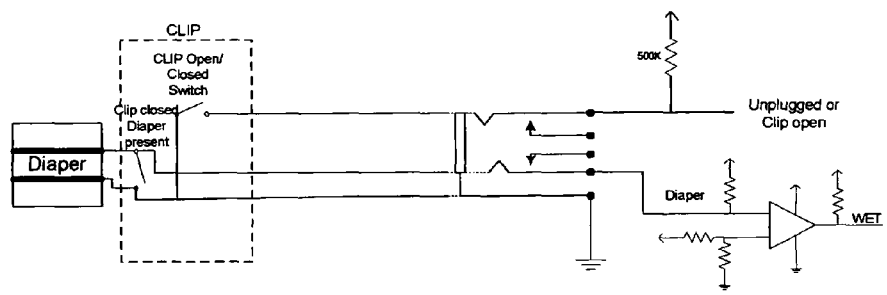
FIG. 6 representatively shows a schematic circuit diagram of sensor detectors that can be employed with the present invention.
Figure 6:
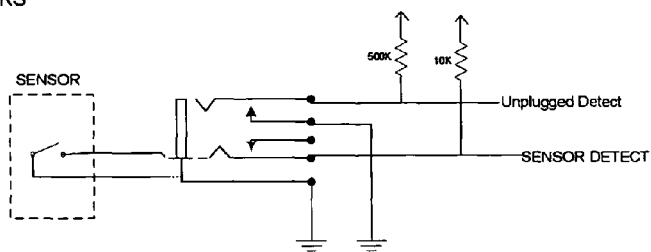

The patient module is a CMOS based RF design which is used to both collect and transmit the patient information to the host. The patient module consists of a small 2×2.5 inch case which contains the electronics as well as ports which permit input from the patient. The heart of the patient module is the logic chip. The patient module uses a Xilinx PLD, Coolrunner, 128 macro-cell. Each of the patient module inputs goes into the xilinx chip. The inputs for the patient module are: 1) visit; the visit is activated by a magnetic reed switch. This is to ensure that the caregiver has to be present at the patient location. If there are patient items in the queue, a visit will clear those items temporarily. If they have not corrected the item in the queue, then the item will immediately return to the queue. If no patient items are in the queue, then activation of this switch is considered as just a visit. The visit is transmitted according to the process that will be described later in the transmit section. 2) Wet; a wet signal is generated by way of a comparator op amp. When the resistance in the disposable diaper drops as a result of wetness, this resistance change is measured at the inputs of the comparator and causes the output to switch low. The threshold of the op amp is determined by a resistor divider network as shown in FIG. 4. The low output is detected by the xilinx chip where it activates a send. The patient name is transmitted to the queue and remains there until a dry diaper is on the patient and the visit button is wanded. This then clears the queue and annotates the patient history that they have been changed and are now dry. 3) Low Battery detector. This circuit is also a comparator op amp. A trigger voltage level is placed on one side of the comparator. The other side of the op amp is tied to VCC. When the voltage level provided by the battery drops to the level of the trigger voltage, a low is presented at the output of the comparator as shown in FIG. 5 A low battery signal is detected by the xilinx and initiates a low battery message to be transmitted 4) Call Button. The call button is patient activated. It is used to notify the caregiver that something is required by the patient. When the patient pushes this button a high is sent to the xilinx chip and transmitted. The patient name and request for assistance is placed into the queue.

When the patient is visited by the caregiver, the caregiver passes his token across the face of the patient module and the request for service is replaced by a notation in the patient queue that he was visited. It also denotes time and date of visit 5) 911 call. This button is pushed by the patient when they think that an emergency has arisen. It can be programmed or left disabled depending on the cognizance of the patient. This differs from the call button in that when this transmission is received by the management system, it appears in bold and red and in much larger print which flashes and beeps. It continues this transmission until cleared by a check from the caregiver. 6) Movement indicator. This records the number of times that a patient rocks and the intensity of the rocking. The software counts each transmission and when the number of movements in a specified time period reaches the patient programmed amount, the patient is sent to the queue. The intention of this is to monitor how agitated a patient is becoming prior to them trying to get out of their chair or stand up or falling. As with other patient module indicators, it is reset and removed from the queue by a caregiver visit; who is help the person readjust themselves, or perhaps stand for a bit or take a walk. The objective is to predict and prevent a fall. 7) Fall indicator. If a patient should happen o fall, this reed switch opens to indicate that they have fallen and need assistance. This transmission as for the 911, flashes, is in red, is larger print and beeps to assist in immediate recognition. 8) Location indicator. This inputs comes from sensory locators on the patient which when passing through monitors in a restricted area sends a high to notify that the person has left or entered a restricted area. As with the 911 and fall indicator, this indicator to the queue is in bolded, caps, red and flashing font with beep. The transmission sequence for the patent module is as follows: The first 4 bits are sync bits. They are hard coded and should be high, low, high, high.

The next 3 bits are ID bits. These bits are what you will use to determine who is sending the data.

001 Patient
010 Caregiver
011 Nurse
100 Physician

When you decode these bits, you will use them to determine which table you will address to decode the remainder of the data in the stream.

The next 9 bits are patient ID bits.

000000001—will be patient 1. These bits are binary and will be tied to the patient file. All data in the data stream will be tied to the patient file by way of this identifier.

The next 5 bits are tied to the caregiver modules. They have no application to the patient module and therefore they remain zeros.

The next 12 bits are the service bits. These bits are not binary. Each bit represents a service.

| | |
|---|---|
| 100000000000 | Assisted with transfer |
| 010000000000 | Bathed |
| 001000000000 | Cleaned Bathroom |
| 000100000000 | Bed Made |
| 000010000000 | Assisted in Dressing or Hygiene |
| 000001000000 | Footcare |
| 000000100000 | Incontinence Care |
| 000000010000 | Linens Changed |
| 000000001000 | Oral Care |
| 000000000100 | Showered |
| 000000000010 | Therapy |
| 000000000001 | Toileting |

Any or all of these bits can be simultaneously transmitted and each service then has to be recorded in the file for the patient ID which accompanied the transmission.

The next 12 bits are not used and remain in the zero state.

Any or all of these bits can be simultaneously transmitted and each observation then has to be recorded in the file for the patient ID which accompanied the transmission.

The last 3 bits are end of transmission bits. We should verify, sync and end of transmission bits to be sure we have everything.

Figure 14:
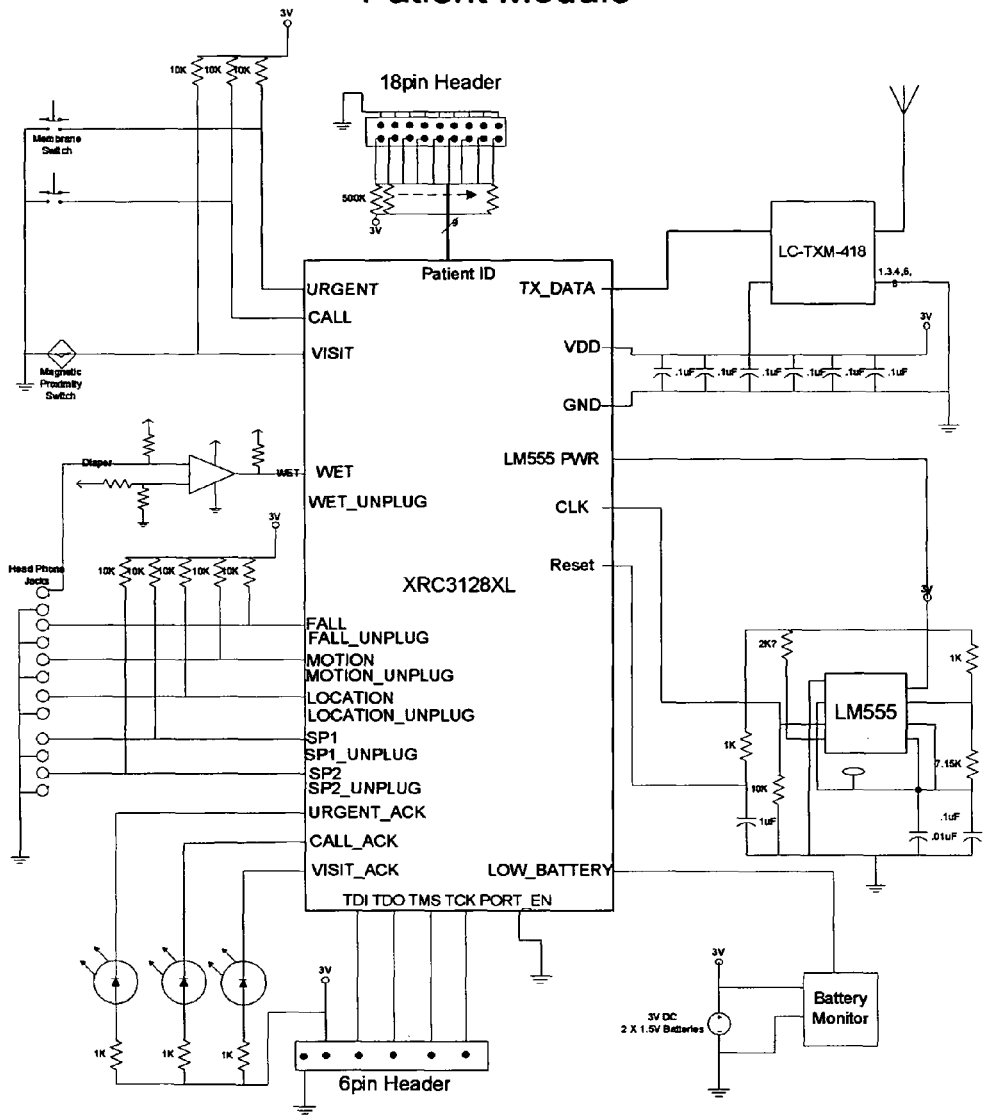
FIG. 14 shows a circuit schematic of a patient unit suitable for use in the present invention.

FIG. 14 is a schematic circuit of the patient. This module is part of the assisted living/elderly patient caregiver monitoring system.

The patient module consists of several different sensors that when triggered send a message via RF back to a computer that logs the event, the patient ID and the time the event occurred. One of the sensors is a wet detection sensor. The sensor part of this module is identical to the infant sensor and will not be covered again. The interface to the comparator for the RF notification circuit is xilinx CPLD. A CPLD is a programmable logic device that can be programmed to perform a specific function. The CPLD in the RF Notification monitors all the sensor inputs, including the wet event sensor, when it detects an event it logs the event. Once the event has been logged it transmits to the base station the even that has just occurred along with an ID so the computer can attach the event to a specific person. The transmission range of this system is dependant on a number of factors; distance, line of sight, height placement of transmitter and receiver, battery level in the transmitter, transmitter/receiver frequency.

The critical component to the comparator senor system is the selection of the reference resistors. The reference resisters determine the sensitivity of the system and ultimately the sensor ability to accurately detect a wet event. One concern with this sensing method is the ability for the sensor to discern between a wet event and wetness cause perspiration. With the correct selection of the resistors in the reference resistors network this false detection could almost be eliminated.

Testing required to determine these values is as follows:

100s of resistance measurements need to be made on diapers as they are being wet.

Resistance curves versus wetness need to be generated from test data

Resistance measurements need to be made on diapers that our not wet but the wearer is perspiring. A perspiration simulator needs to be develop to accurately modal perspiration so higher volume tests can be conducted in the lab.

Resistance curves versus perspiration need to be generated from test data

With these results different resistor networks can be chosen implemented and tested to determine if they are correct.

Adaptive Wetness Sensing Technology

This new sensing circuit is an improvement over simple comparator based systems and eliminate the false alarm detection of perspiration. The difference between this wet sensing technology and the simple comparative wet sensing units is the ability for the unit to change it's dynamic range of operation by selecting different values up pull up resistance or sample the actual voltage across the diaper and record the rate of change of voltage to determine if a wet event has occurred.

Dynamic Resistance Selecting Comparator Based Sensing Technology

The ability to dynamically change the comparator pull up measurement resistance allows the sensor operate through numerous wet events and give the unit the notification section of the unit the ability to uniquely feedback to the user which wet state the sensor is currently. This directly translated to a rough saturation level in the diaper.

Figure 9:
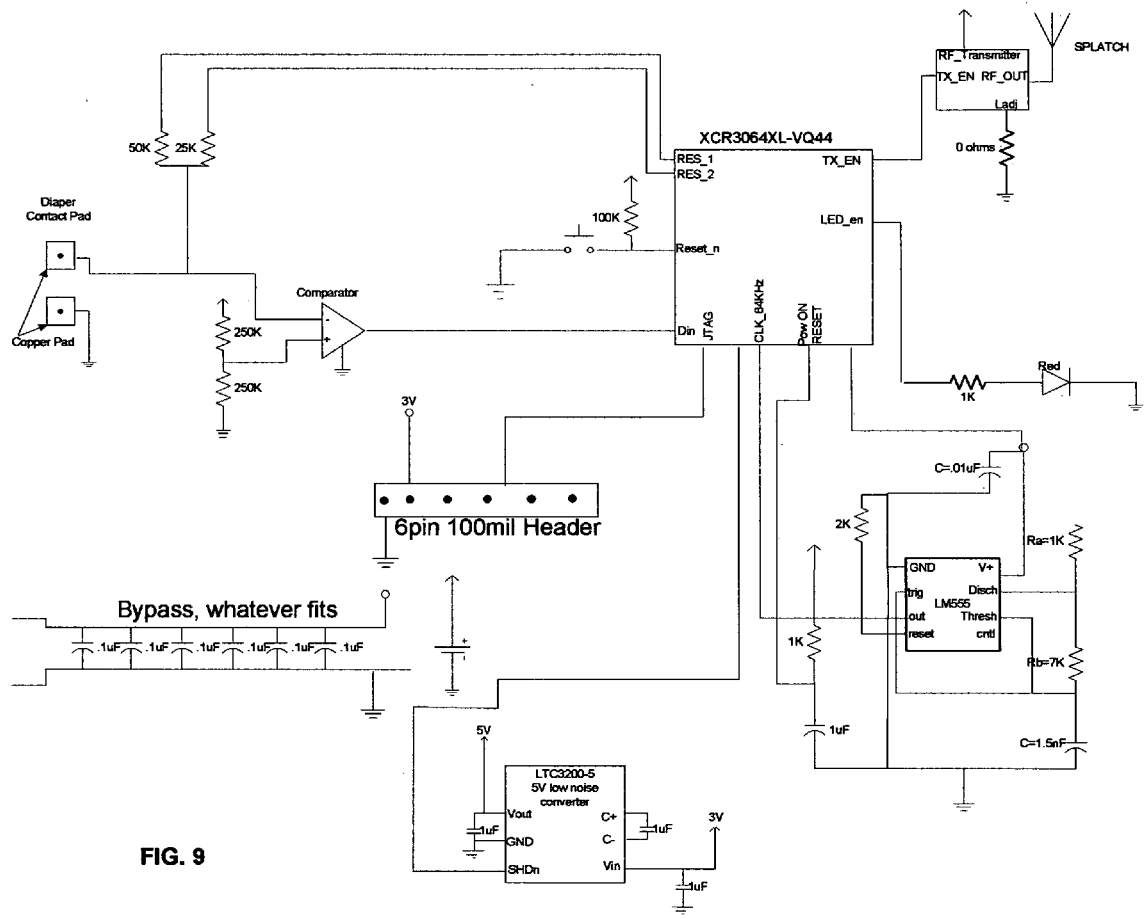
FIG. 9 representatively shows a schematic circuit diagram of a dynamic resistance selecting comparator based sensing technology circuit that can be employed with the present invention.

The sensor currently built with this type of sensing feature is illustrated in FIG. 9. The two resistors hanging off of the minus input of the comparator and connecting into the Xilinx is what makes this unit unique. RES_1 and RES_2 outputs of the Xilinx are Tri state controlled output of the Xilinx. This gives the sensor the ability to cycle through the resistance values changing the amount of wetness it will take in the diaper for the sensor to trigger: RES_1=50K and RES_2=25K in this schematic. When the sensor is reset and placed onto the child RES_1 output is driven high and RES_2 is in a tri-state. This will give place a 50K pull up value on the input of the comparator. The diaper will have to reach a resistance of this level before it will trigger. At the time the child wets the sensor will trigger and in the case of the Wireless infant unit it will send a message to a receiver notifying it of the wet event and also that it was the first wet event of the current diaper. After the notification the sensor switches RES_1 to tri_state and RES_2 turns on. In the case of the Wireless Infant unit this will place 25K pull up on the diaper sensor input. This will require the diaper resistance to drop to 25K before it will trigger which will result in the second wetting of the diaper. Once this level is triggered the same notification mechanism is triggered but this time the unit sends to the receiver the message that RES_2 has been triggered thus this is the second wetting. After the notification period the sensor turns on both RES_1 and RES_2 placing the parallel combination of the two resistances on the input of the comparator. In the case of the Wireless infant unit this will be approximately 16K. This level will not trigger until the third wetting. Again the notification until will send a message that the diaper has again been wet and what that the resistance values. In the case of the Infant Wireless unit it is deemed that at this point the diaper is saturated and needs to be changed so it will periodically notify the caregiver of this and will continue to do so until the diaper is changed and the sensor unit is reset.

The Number of resistances a unit can cycle through is really up to the sensing environment the sensing unit is operating in. The two resistor Wireless infant unit could have very easily had several more resistances giving it a much greater dynamic range. Also the order in which the resistance values are cycled through can also be change, i.e. after the initial wetting the resistance selection algorithm could have left RES_1 on until it triggered for a second time. The possibilities are endless making this a very power full sensing unit.

Figure 10:
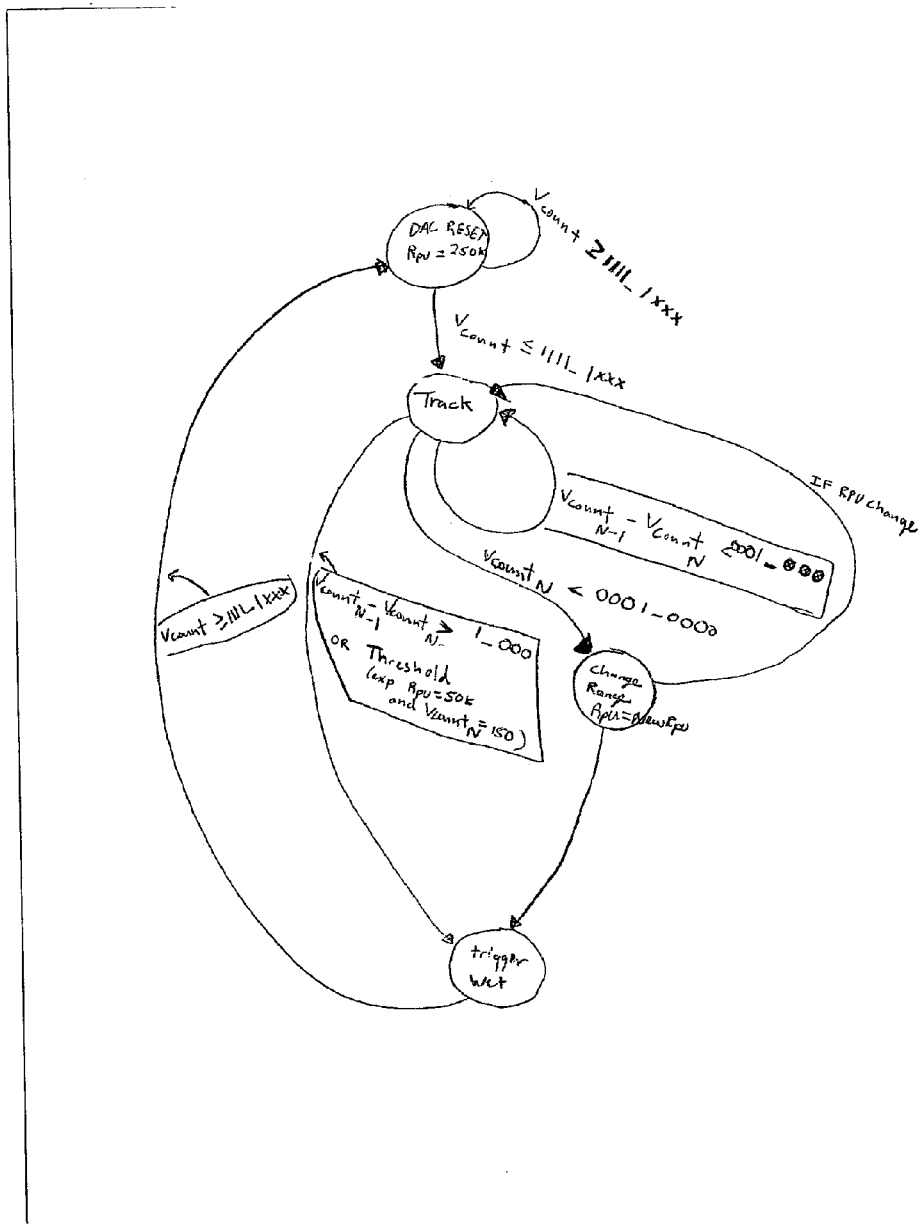
FIG. 10 is a diagram of a state machine algorithm of dynamic resistance selection in accordance with some embodiments of the invention.

FIG. 10 shows a rough hand sketch drawing of the algorithm just described above but in a pictoral state machine format. The computer program listing appendix Appendix 1 of this Document contains the VHDL that will run in the Xilinx.

Dynamic Resistance Selecting Rate of Change Measuring Based Sensing Technology

Figure 11:
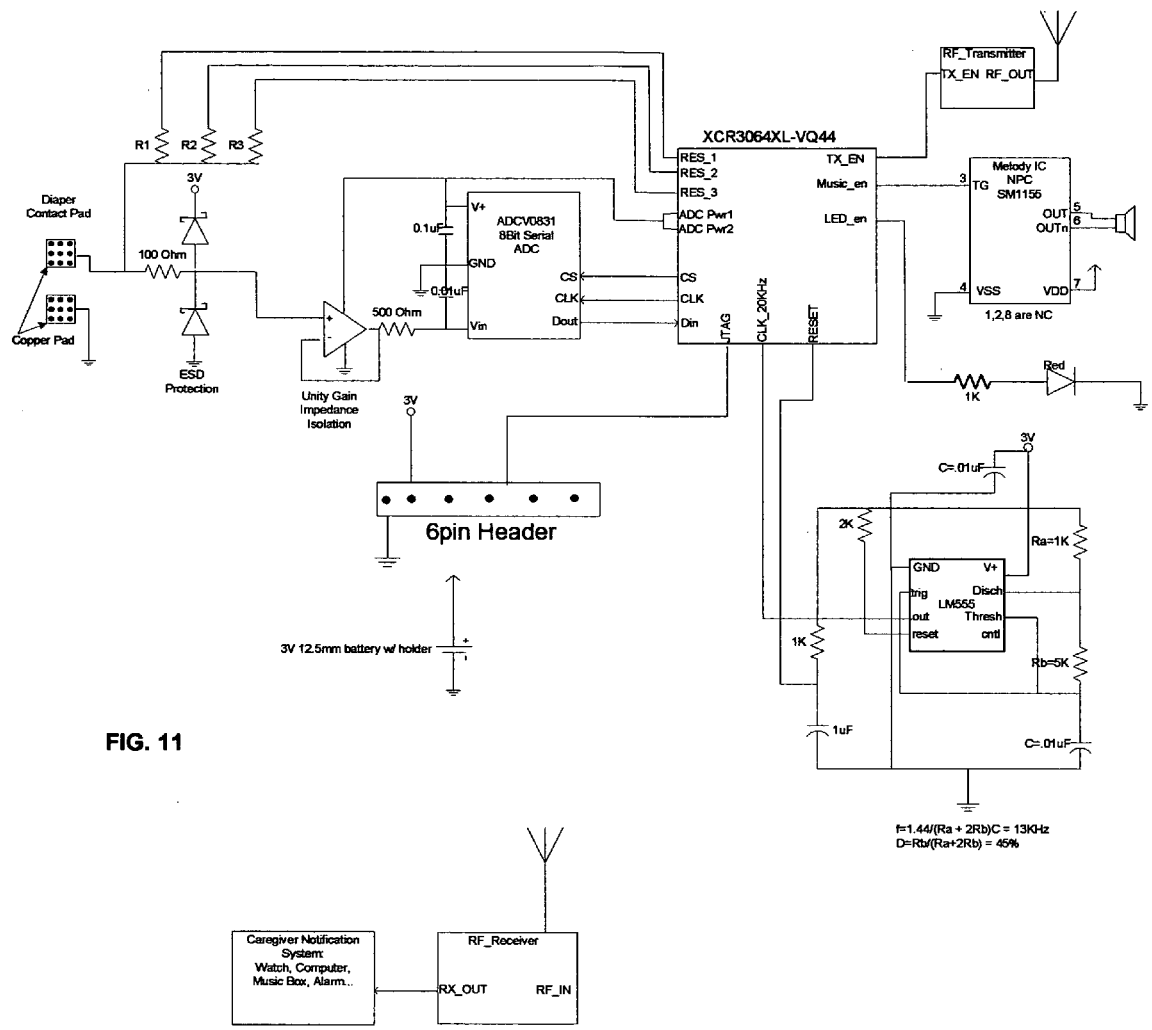
FIG. 11 representatively shows a schematic circuit diagram of a real-time, adaptive wet sensing circuit that can be employed with the present invention.

This technology tracks the wetness by measuring the voltage across the diaper and only trigger an event if the rate of change of the wetness measure is greater then a threshold value. It also enables that an absolute level be set so that if the rate of change is never detected that it will select another resistance pull up value giving it another dynamic operating range. FIG. 11 illustrates this circuit.

The adaptive circuit will constantly measure the resistance of the diaper. Converting the resistance of the diaper to a voltage level and sampling the voltage level of this circuit with an Analog to digital converter replaces the comparator sensing circuit. The old comparator based version only returned and absolute value to the sensor event manager, wet or not wet. This new circuit will pass it a voltage value that represents a resistance value. It can use this new value and compare it to the previous sampled value to determine if a wet even has occurred. The threshold value can be set such that small changes in the voltage values will not result in the triggering of a wet event only a large change. This will allow the system to filter out perspiration but still trigger on the wet events.

This unit also has the different pull up resistor allowing the sensor to cycle through them giving the Analog to Digital Converter larger dynamic ranges in which to operate.

The notification system for this circuit can be anything the customer likes. It can include but is not limited to the notification devices discuss in the introduction and implemented in our current device.

The real power of this system and algorithm will be realized when we convert our units from CPLD based controllers to micro controllers that have built in Analog to Digital Comparators.

Microprocessor or ASIC Based Adaptive Sensor Technology

Eventual replacements of the Xilinx CPLD circuit discussed above will be more cost effective Micro controller based or ASIC based sensor units.

Figure 12:
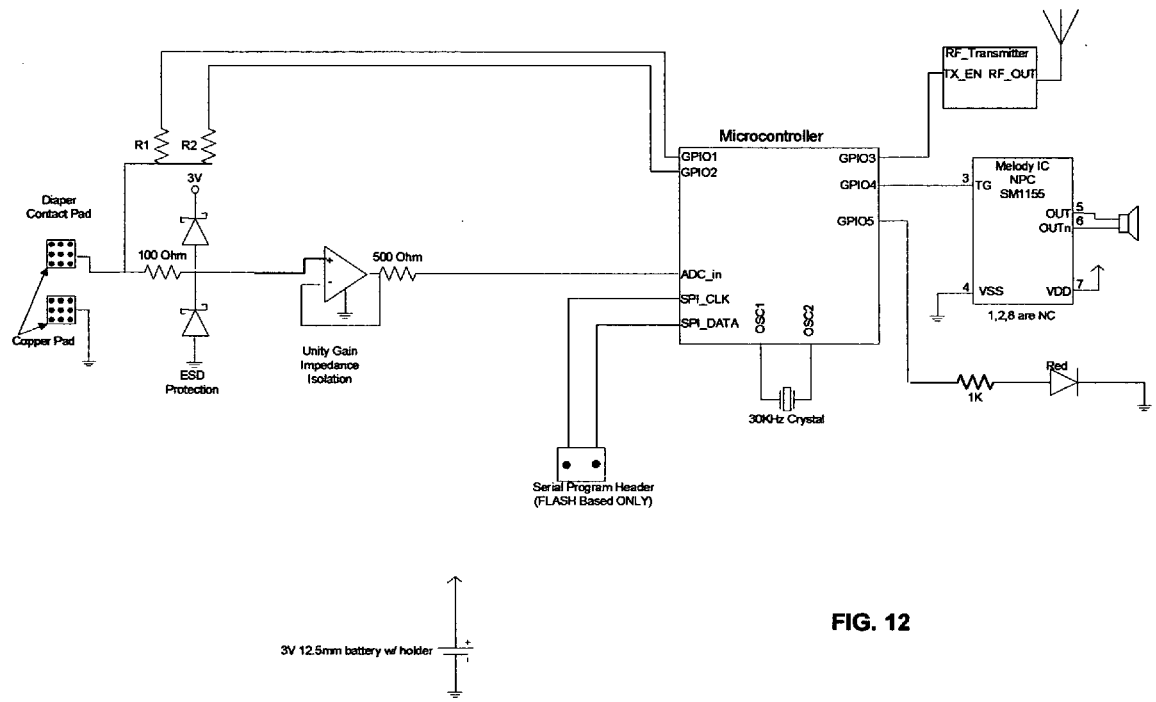
FIG. 12 representatively shows a schematic circuit diagram of a micro controller-based real-time, rate of change wet sensing circuit that can be employed with the present invention.
Figure 12:
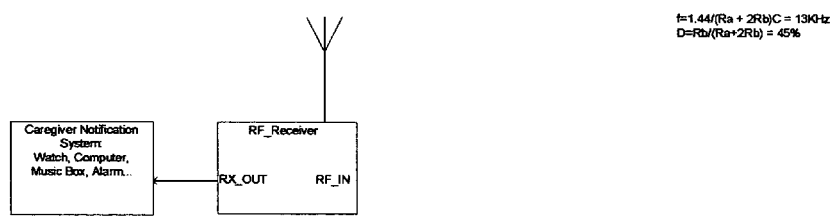

The control algorithms, resistance selection technology and rate of change sampling technology will still be implemented just with a different controller type. FIG. 12 is just one illustration of a microprocessor based sensor unit.

Notification Circuits

Notification of the wet event can include but is not limited to: Blinking LEDs, Voice Record and Playback, Vibration, Buzzer, Melody, and Daycare Software. One embodiment of a remote notification system is the day care monitoring system.

Day Care Monitoring Software

A PC equipped with a Receive antenna tuned to wireless infant units and the Day Care Monitoring software creates a very powerful Notification and Feedback system.

Mommy Wireless Unit

Figure 13:
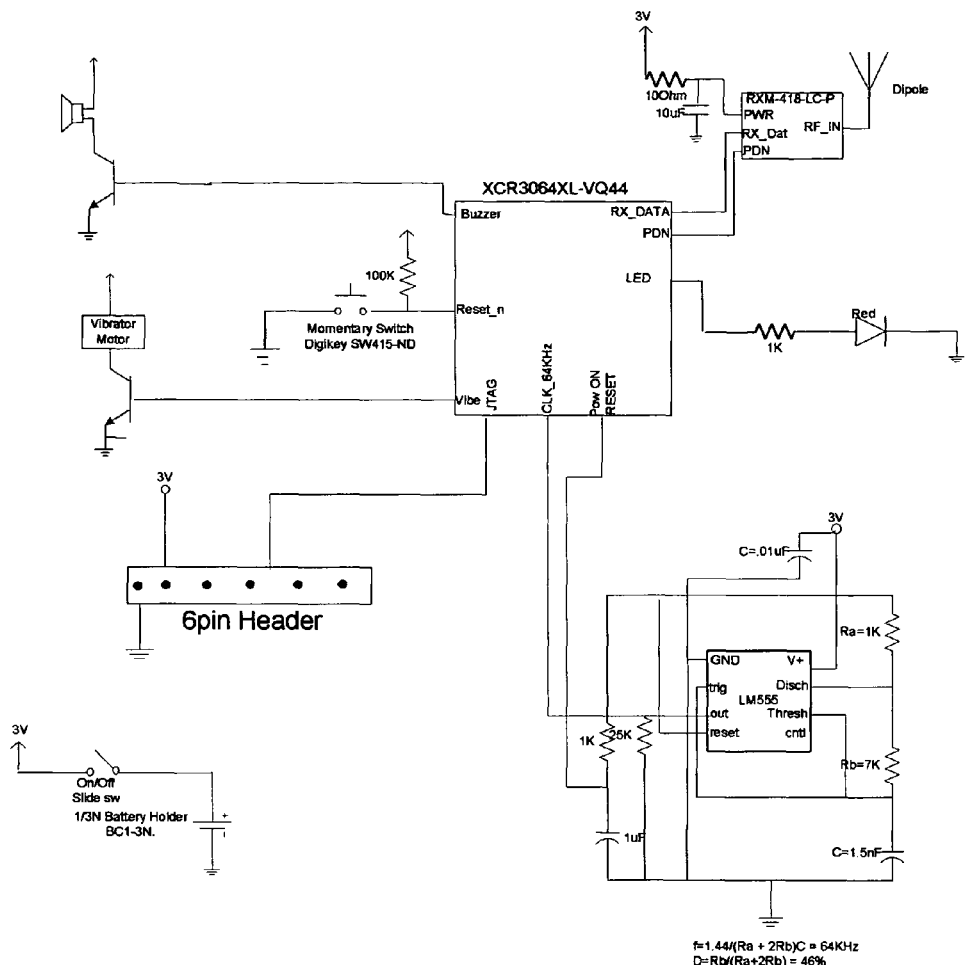
FIG. 13 shows a circuit schematic of a mommy unit suitable for use in the present invention.

The Mommy unit is Frequencies First Mobile Wireless receiver module. It is tuned to receive messages from the Wireless Infant Units. FIG. 13 is a top level schematic of this unit. It has three feedback mechanisms built into it. They include LED, Buzzer and Vibrator Motor. The unit will receive messages from the Wireless infant unit and based on the resistance values encoded into the message will generate a unique feedback to the mother/father of what wet state the diaper is in. The computer program listing appendix has the detailed VHDL software used in operating this ciruit.

Caregiver Module

Figure 7:
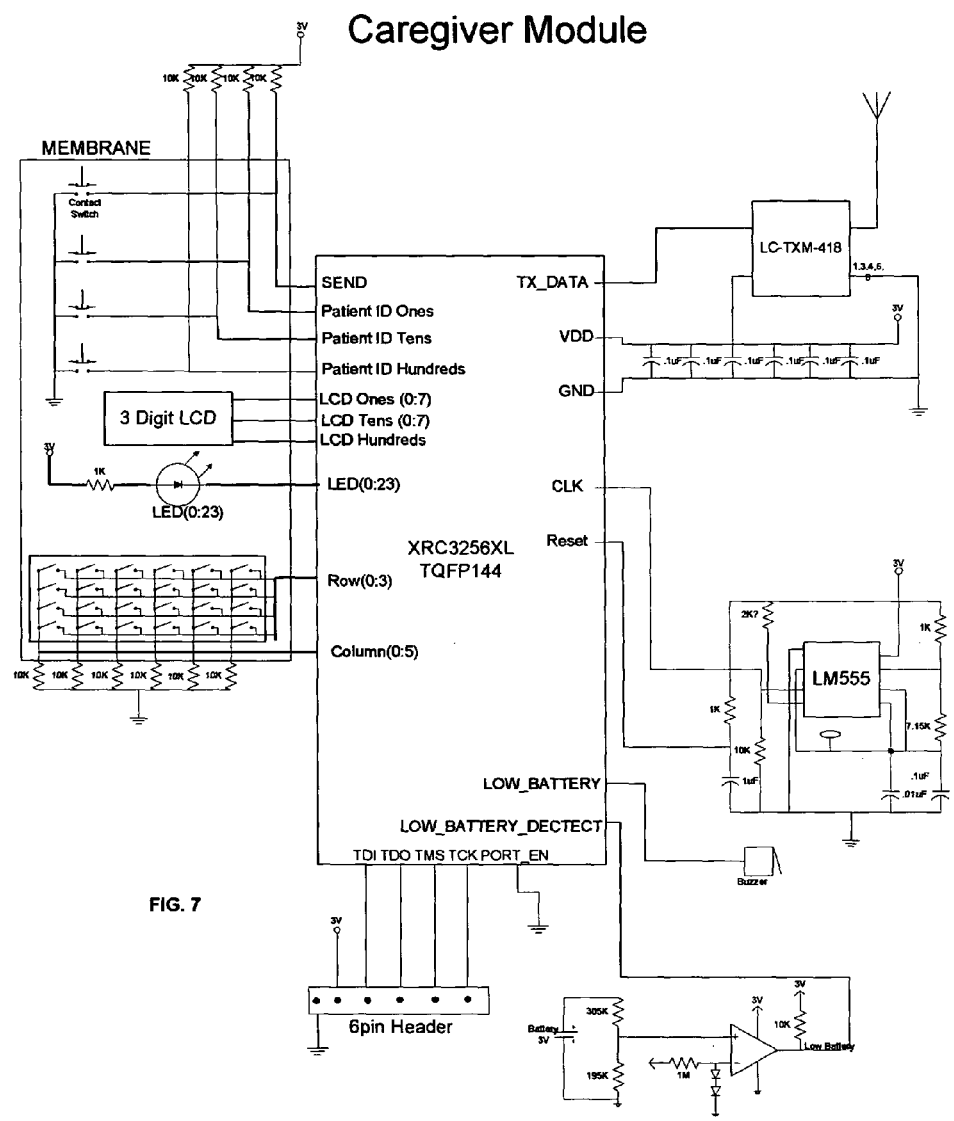
FIG. 7 shows a circuit schematic of a caregiver unit suitable for use in the present invention.

The caregiver module is shown in FIG. 7. It can be implemented in standard handheld and similar computing device. The Caregiver module consists of 12 buttons of services and 12 buttons of observations. It has an on/off switch to conserve power when not being used. It has a send button which is used to initiate a transmission after selecting the appropriate services and/or observations. Any combination of services or observations can be selected. Each of the service and observation buttons is a toggle. Push on and then push off. When one of the observations or services is selected, the associated LED becomes lit. When it is deselected it goes out. When a transmission has been sent, any selected services or observations are blanked out. The module also has a coded serial number. At shift change or when the module is given to another caregiver, the caregiver registers the module serial number during their login. Any transmissions made by that module indicates that caregivers name in the annotated patient history for all care admistered. The patient ID is entered by pressing the buttons below the Digital Patient ID display. There is a button for the ones, tens and hundreds columns. Pushing the button below the appropriate digit causes the digit to increment by 1. The digits do not carry over. When a transmission is made from the caregiver module, the patient ID is also transmitted. Each of the services or observations selected in the transmission is annotated to the patient history along with a date/time stamp and the caregiver name or ID. The caregiver module also has a visual transmission LED to indicate when a transmission is sent. The core of the caregiver module like the patient module is a xilinx chip. The operation and function of the chip is given in the xilinx module. The caregiver module transmission codes are as follows: The first 4 bits are sync bits. They are hard-coded and should be high, low, high, high.

The next 3 bits are ID bits. These bits are what you will use to, determine who is sending the data.

001 Patient
010 Caregiver
011 Nurse
100 Physician

When you decode these bits, you will use them to determine which table you will address to decode the remainder of the data in the stream.

The next 9 bits are patient ID bits.

000000001—will be patient 1. These bits are binary and will be tied to the patient file. All data in the data stream will be tied to the patient file by way of this identifier.

The next 5 bits are tied to the caregiver modules. They are labeled 1-X where X is the number of modules in a given facility. We will need a key in the software that the facility will press to activate software that will ask who a specific module belongs to.

00000 is an assigned value. 00001 would be module 1. If the 3 ID bits above are 001 for the patient, these bits are of no significance. If the 3 ID bits above are 010, the bits will indicate what employee has sent the transmission.

When the employee hits the sign-in key, they will be prompted to enter their name and the module ID. This data will remain set until the next person signs in for that module. All transmissions for that module will be logged with that person as the provider. A database that tracks all of the service rendered by that provider with date needs to be recorded. This would allow the nursing home to monitor the work done by each employee in the facility.

The next 12 bits are the service bits. These bits are not binary. Each bit represents a service.

| | |
|---|---|
| 100000000000 | Assisted with transfer |
| 010000000000 | Bathed |
| 001000000000 | Cleaned Bathroom |
| 000100000000 | Bed Made |
| 000010000000 | Assisted in Dressing or Hygiene |
| 000001000000 | Footcare |
| 000000100000 | Incontinence Care |
| 000000010000 | Linens Changed |
| 000000001000 | Oral Care |
| 000000000100 | Showered |
| 000000000010 | Therapy |
| 000000000001 | Toileting |

Any or all of these bits can be simultaneously transmitted and each service then has to be recorded in the file for the patient ID which accompanied the transmission.

The next 12 bits are the observation bits. These bits are not binary. Each bit represents an observation.

| | |
|---|---|
| 100000000000 | Bedsores |
| 010000000000 | Bleeding |
| 001000000000 | Change in Activity |
| 000100000000 | Chest Pain |
| 000010000000 | Cold Symptoms |
| 000001000000 | Dehydration |
| 000000100000 | Depression or Confusion |
| 000000010000 | Dizziness |
| 000000001000 | Fall |
| 000000000100 | Hazard exists |
| 000000000010 | Loss of Appetite |
| 000000000001 | Nausea or Vomiting |

Any or all of these bits can be simultaneously transmitted and each observation then has to be recorded in the file for the patient ID which accompanied the transmission.

The last 3 bits are end of transmission bits. We should verify, sync and end of transmission bits to be sure we have everything. Each transmission sends the entire bit stream. Only selected bits are 1's and therefore invoke an annotation to the patient history.

Xilinx Chip

The xilinx chip controls all of the inputs and outputs for both the patient module and the caregiver module. It also provides all of the appropriate signal manipulations and processing. It is powered by 2 1.5 volt batteries or one 3V Lithium ION flat battery. The heart of the processing is in that the transmission speed is set by the external clock input into the xilinx chip. This clock determines the rate of the shift registers in shifting out the data to the transmitter. After logic evaluation of appropriate input signals, the data is locked into shift registers. Each of these registers in turn, shifts the bits to the transmit chip. Zeros to clear each register are shifted into the registers upon the start of the send signal. Programming for the xilinx chip is shown at the end of this document.

Diaper

Figure 8:
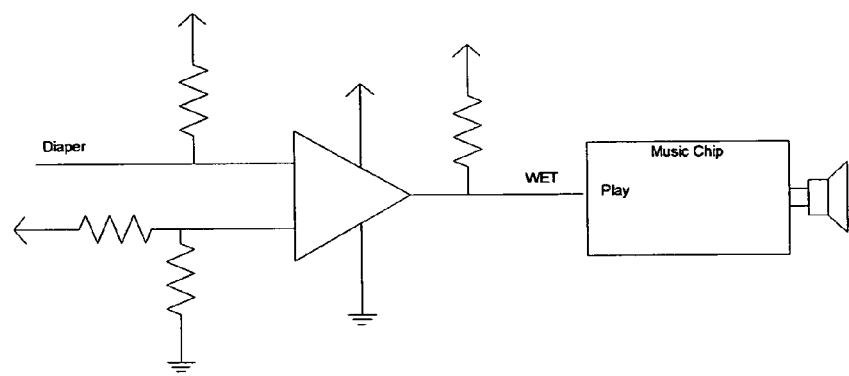
FIG. 8 representatively shows a schematic circuit diagram of sensor detectors that can be employed with the present invention.

The diaper is an integral part of the patient system and also for the infant system. The purpose of the diaper is to sense an appropriate level of wetness and provide a means of measuring that wetness. The system consists of two metal strips placed in the lining of a diaper. Both the dimension of the strips and distance between the strips are calculated to provide appropriate and uniform resistance changes when they become wet with urine. The saline urine forms a resistive link between the strips of metal and this resistance is input into a comparator circuit to produce an appropriate output. The metal used in our application is aluminum because of its cost and ease and variety of manufacture. It has a mylar support backing to provide additional strength during manufacture and application. However, any metal capable of sensing and providing a changing resistance could be also used. Besides the variations in metal, one could also use any conductive fiber which would provide the same function. We have successfully used combination stainless steel and nylon thread in a sewn application which indicates the wide variations capable of providing the same input to the comparator. As far as the diaper goes, it can be disposable or non-disposable and can include any number of materials used in the care of incontinent elderly. The sensing circuitry for the wetness control consists of a resistor divider network on one side of a comparator with the serial input of the diaper on the other. Gnd is supplied on one side of the sensor in the diaper and the other side is connected to the comparator. When wet, the line is pulled to ground with a resistance drop equal to the width of the conductor, separation, and degree of wetness. The comparator resistance is set by generated resistor curves from experimental data. The comparator output feeds into either the patient monitor or in the case of an infant detector, the comparator is embedded into the clip. In the case of the infant detector, the comparator triggers either an audible alarm or a visual LED. See the circuit schematic as shown in FIG. 8.

Diaper Clip

The diaper clip or diaper contact is a small rectangular PC board with two rows of six pins each angled at about 165-170 degrees (so not quite straight up and down) which have a center point corresponding to the yellow lines (sensor strips) on the diaper liner.

The pins extend slightly through the back of the PC board, such that when they are soldered they will form pin prick contact points. Each of the slightly angled rows will contact one of the aluminum traces on the disposable diaper. The slight angle to the rows will permit the fastener to be slightly off and still contact somewhere on the row of pins.

There is a wire attachment to each of the row of pins so that we can connect these wires to the patient sensor or in the case of the infant diaper sensor, the entire infant module is built on the same pc board and no wires are necessary since it is integrated directly into the sensor module.

Now comes the tricky part. The center of the rectangle, between the 2 rows of solder pin contacts, needs to have a hole drilled to fit a snap. For now it can be a metal snap (the same kind used on clothing. The top of the snap needs to fit flush with the top of the board so that when it is snapped onto the other snap, the two pieces fit snuggly. For the finished molded product, the snap will be molded from the plastic used to encase the connector board. I envision that the PC board will be molded directly into the plastic snap which will be shaped like a hinge, having 2 sides as described below. Both sides of the snap or fastener will be molded components and most likely will not be metal as is the prototype.

The snap will probably have to be epoxyied into the board. Then there needs to be another rectangle of the same dimension which forms the other side of the slip. It needs to have the same hole array, but these holes are left empty so that the soldered point pins can actually go into these holes when the two sides are snapped together. We will work on some kind of a hinge mechanism after we get this part working. This other side will also have a hole drilled into the middle, between the two rows of angled holes which will have the other half of the metal snap epoxyied into it. For the molded finished piece, not the prototype, this second board and female snap will be molded directly into the plastic hinged assembly. For the infant diapers, it will be self contained and will be disposable pretty much. The unit would most likely just be sold with a package of diapers. For the nursing home and assisted living centers, and of course for personal home use, the diaper clip or sensor clip would most likely be associated with a transmitting unit, or patient module.

Here is the way, the whole part will function. The diaper has the two metal strips running down the inside. Where these two strips come up to either the front or the back of the diaper, the plastic liner is folder over on itself, so that the metal strip is exposed on both sides of the diaper (folded over). Over this folded sensor, the clip is placed, one side on one side of the plastic, and the other snap and side on the other side of the plastic. When the two sides are snapped together, it will actually have the plastic liner snapped between the snaps. This will hold the clip firmly onto the diaper, unless it is pulled so hard that the plastic is torn from the liner, with the contact points connecting with the sensor strips in the diaper and transmitting the diaper condition to the modules.

Xilinx Code for the Patient and Caregiver Module

Addendum to the diaper and diaper sensor used for all applications, both infant, and adult and used in all applications including wetness sensing, toilet training, and enuresis.

In order to manufacture diapers under assembly line conditions, it is necessary to provide the sensing material in a manner that provides both the electronic sensing capabilities, but also a manner of applying that is cost effective and durable enough to withstand moving assembly line conditions. Prior art deals with the function of this material as wires, and metal, but these are just placed as sensors in the diaper and don't account for the difficulties of manufacturing. Many even suggest in their patents the difficulty of placing these sensors into diapers one by one. This addendum is to clarify the methodology chosen by Frequency to deal with the conditions necessary for manufacturing. Although explained in the prior provisional patent, it was felt that the explanation was not clear enough to remove any doubt of the application and intent and so it will be clarified in this filing.

The metal foil used in this application differs from prior art in that it is a continuous line of sensing film extending the length and width of the diaper depending on the application and the equipment being used. It is a laminated film of metal, in this case aluminum, and a backing which provides both tensile strength and permeability. The ideal application is a laminate that is perforated or porus providing both strength, and insulation. This sensing layer is placed in the diaper at any level considered applicable, but would be most appropriate beneath the absorbent pad and exterior imperiable layer. There are some applications where it would be appropriate to contact this sensing strip from the exterior of the diaper. In order to do this, the strip would run past a location in the exterior of the diaper where holes have been placed in the layer providing electrical contact exterior to the diaper. Where clips or other mechanical connectors are used, these holes are not necessary and the clip or mechanical device provides sufficient contact to the strip conductors. These strip conductors can but do not need to be adhesive coated. The manufacturing flow of the diaper places sufficient adhesive into the diaper lining to provide the necessary adhesion for the sensing strips. In this manner, these strips match very well with existing processing flows.

In the prior filing we indicated that we had done trials on a stainless steel thread that, could be sewn into a sensing pattern or substrate. It could just as easily be placed into the assembly line like the metal foils described above without any necessity for sewing. It could also be multidirectional depending on the sophistication of the assembly line equipment.

The actual attachments of the electronics to the sensing strips is by standard electrical contact methods and is outside the scope of this filing. Suffice it to say that all types of connectors may be utilized including but not limited to: snaps, clips, direct solder, fusion, friction bonding, surface contacts, puncture, and stitched and could include any combination of connections such a snaps and stitched.

Sensing Electronics

This filing will also describe improved methodologies for the electronics used in sensing wetness. One of the inherent problems with sensing wetness is the wide range of wet conditions. These are caused from differences in habitation (humid areas verses dry), activity, differences in body types, living conditions, etc. Sweat is a major cause of problems giving inconsistent readings, false readings, etc. These differences are why no system is currently on the market because no product developed to date has been capable of giving 100% accuracy.

Our methodology is significantly different from any prior art. Prior art uses a resistivity threshold trigger, a capacitance change, etc. Our embodiment determines a baseline and then consistently monitors that baseline making realtime corrections until an event occurs that is a large enough change from this realtime baseline to be considered a valid state change (wet condition). This concept of establishing a baseline and then continuing realtime monitoring and changes to that baseline until an event occurs is novel.

The baseline is established by a automated routine which the electronics performs when the diaper is attached to the electronics. This baseline is monitored on a preprogrammed interval which can adapt and change depending on realtime changes which are occurring. In otherwords, the system is a smart monitor capable of sensing and adapting its readings to realtime baseline changes. These realtime baseline changes allow for resistance changes without giving false readings that a wetness event has occurred. Only when the realtime delta exceeds a predetermined step function does the system recognize a wet event.

All known embodiments of notification when a wetness event occurs would then be applicable. These are already established electronics and are prior art. They would include but not be limited to the following: LED, buzzer, beeper, alarm, wireless transmission, wired transmission, pizzo, modem, direct internet connection, etc., This methodology can be local in the diaper or medium where wetness is being measured or can be remotely transmitted data that is processed by an algorithm located on an external device. Two example of the electronics used in this application is shown below along with a sketch of the algorithm state machine.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A patient monitoring system for detecting wetness in an article, comprising: a. a sensor means configured with a diaper, wherein said sensor means is adapted to detect a wetness event occurring within said diaper; b. a monitoring unit comprising a monitoring system controller means in communication with said sensor means, wherein said monitoring system controller means monitors said sensor means and generates data associated with detected wetness events relative to said diaper so that said monitoring system controller means can detect a variety of wetness conditions and discern between valid wetness events and false or erroneous wetness events caused by static, said diaper providing attaching means for removably attaching said monitoring unit to said diaper; c. a notification means for informing of the said data associated with detected wetness events relative to said diaper, and the notification means being activated by the output of the monitoring system controller means; d. where in said sensor means comprises 1) a laminated metal film, having a front side and a back side, said laminated metal film extending the entire length of the diaper in two strips; 2) a mylar material attached to said back side of said laminated metal film thereby providing tensile strength and permeability to the said laminated metal film; 3) where said front side of said laminated metal film is adhesively secured to the diaper.

2. The patient monitoring system according to claim 1, wherein said notification means further comprises a display means configured with said monitoring unit and in communication with said monitoring system controller, wherein said display means is adapted to display said data associated with said detected wetness event and corresponding condition of said diaper.

3. The patient monitoring system according to claim 1, wherein said notification means further comprises a sound generating means configured with said monitoring unit and in communication with said monitoring system controller, k wherein said sound generating means is responsive to the detection of a wetness event.

4. The patient monitoring system according to claim 1, said system further comprising: a data port configured with said monitoring unit and in communication with said monitoring system controller, wherein said data port facilitates communications between said monitoring unit and an external system, wherein said communications include said data associated with said detected wetness event and corresponding condition of said diaper.

5. The patient monitoring system according to claim 1, wherein said notification means further comprises: a. an external display means, configured with said monitoring unit and in communication with said monitoring system controller, wherein said display means is adapted to display said data associated with said detected wetness event and corresponding condition of said diaper; b. a wireless transmitter configured with said monitoring unit and in communication with said monitoring system controller, wherein said wireless transmitter facilitates communications between said monitoring unit and said external display means.

6. The patient monitoring system according to claim 5, wherein said single external Display means in communication with said wireless receiver is capable of receiving communications from a plurality of said monitoring units.

7. The patient monitoring system according to claim 5, further comprising: a. a recording means configured to record a plurality of events associated with a caregiver visit to the wearer of said diaper, wherein each recorded event represents at least one of the following: an observation of the condition of the wearer of said diaper, a service provided to the wearer of the diaper, the same and identifying information of the caregiver, and the name and identifying information of the wearer of the diaper; b. a caregiver unit comprising a caregiver system controller means in communication with said recording means, wherein said caregiver system controller means is operatively associated with said recording means and generates data associated with recorded events relative to a caregiver visit.

8. The patient monitoring system according to claim 7, further comprising a data port configured with said caregiver unit and in communication with said caregiver system controller, wherein said data port facilitates communications between said caregiver unit and an external system, wherein said communications include said generated data associated with said recorded events relatiave to a caregiver visit.

9. The patient monitoring system according to claim 7, further comprising a wireless transmitter configured with said caregiver unit and in communication with said caregiver system controller, wherein said wireless transmitter facilitates communications between said caregiver unit and said external display unit, wherein said communications includes said generated data associated with said recorded events relative to a caregiver visit.

10. The patient monitoring system according to claim 1, wherein said notification means further comprises: a. an external sound generating means configured with said monitoring unit and in communication with said monitoring system controller, wherein said sound generating means is responsive to the detection of a wetness event; or b. a wireless transmitter configured with said monitoring unit and in communication with said monitoring system controller, wherein said wireless transmitter facilitates communications between said monitoring unit and said external sound generating means.

11. The patient monitoring system according to claim 1, wherein said external sound generations means in communication with said wireless transmitter is capable of receiving communications from a plurality of said monitoring units.

12. The patient monitoring system according to claim 1, wherein said monitoring system controller of said monitoring unit further comprises a means for detecting, a plurality of levels of wetness of the said diaper in real-time.

13. The patient monitoring system according to claim 1, wherein said monitoring system controller of said monitoring unit further comprises a means for determining the rate of change of the level of wetness of the diaper in real-time.

14. A process of manufacturing a wetness sensing article, said process incorporating the sensor means of claim 1, said sensor in two strips integrated into a high speed manufacturing process for diapers, absorbent mats, and absorbent undergarments.

15. A method of sensing and monitoring wetness in an article, said article comprising a sensor as described in claim 1 and incorporated in said article as described in claim 14, said method comprising the steps of: a. configuring of a sensor in an article which can detect wetness; b. removably attaching a monitoring unit to said diaper, the monitoring unit comprising a monitoring system controller in communication with said sensor, wherein said monitoring system controller monitors said sensor and generates data associated with detected wetness events relative to said article so that said monitoring system controller can detect a variety of wetness conditions and discern between valid wetness events and false or erroneous wetness events caused by static; c. sensing a plurality of wetness events in said diaper responsive to said sensor; d. activating a notification of the said data associated with detected wetness events relative to said article.

16. The method as claimed in claim 15, wherein the sensing step further includes detecting a plurality of levels of wetness of the said article in real-time.

17. The method as claimed in claim 15, wherein the sensing step further includes determining the rate of change of the level of wetness of the article in real-time.

18. The method as claimed in claim 15, wherein the sensing step further includes automatically adjusting the sensitivity of said sensor means.

19. The method as claimed in claim 15, wherein the sensing step further includes includes detecting the location of the said article.

20. The method as claimed in claim 15, wherein the sensing step further includes detecting when the wearer of said article moves.

21. The method as claimed in claim 15, wherein the sensing step further includes detecting when the wearer of said article falls.

22. The method as claimed in claim 15, wherein the sensing step further includes detecting when the caregiver visits the wearer of the article.

23. The method as claimed in claim 15, wherein the sensing step further includes detecting when the wearer of the diaper requests the assistance of a caregiver.

24. The method as claimed in claim 15, wherein the activating a notification step further includes displaying said data.

25. The method as claimed in claim 15, wherein the activating a notification step further includes generating a sound.

26. The method as claimed in claim 15, wherein the activating a notification step further includes wirelessly transmitting said data for display on an external display.

27. The method as claimed in claim 15, wherein the activating a notification step further includes generating a sound on an external sound generator.

28. The method as claimed in claim 15, wherein the activating a notification step further includes communicating said data to an external system.

29. The method as claimed in claim 15, wherein said method further comprises the step of recording an event associated with a caregiver visit to the wearer of said diaper, wherein each recorded event represents at least one of the following: an observation of the condition of the wearer of said diaper, a serive provided to the wearer of the diaper, the name and identifyin information of the caregiver, and the name and identifying information of the wearer of the article.

30. The method in claim 25, wherein said method further comprises the step of communicating said recorded event to an external system.

31. The method as claimed in claim 25, wherein said method further comprises the step of wirelessly transmitting said recorded event to an external system.

32. The method as claimed in claim 15, wherein the sensing step further comprises at least one of the steps of: a. detecting a plurality of levels of wetness of the said article in real-time; b. determining the rate of change of the level of wetness of the diaper in real-time; c. automatically adjusting the sensitivity of said sensor means; d. detecting when the wearer of said article moves; e. detecting when the wearer of said diaper falls; f. detecting when a caregiver visits the wearer of the diaper; g. detecting when the wearer of the diaper requests the assistance of a caregiver; h. detecting a false alarm caused by static events by software configured to identify a static event.

* * * * *